United States Patent [19]

Kolber et al.

[11] 4,305,723
[45] Dec. 15, 1981

[54] APPARATUS AND METHOD FOR ABSORBANCE MEASUREMENT AND DATA GENERATION

[75] Inventors: Steven N. Kolber, North Miami Beach; Rodolfo R. Rodriquez, Miami, both of Fla.

[73] Assignee: Coulter Electronics, Inc., Hialeah, Fla.

[21] Appl. No.: 200,144

[22] Filed: Oct. 24, 1980

[51] Int. Cl.³ .................... G01N 35/04; G01N 21/03; G01N 21/13
[52] U.S. Cl. ................. 23/230 R; 356/434; 356/246; 364/498; 422/64; 422/67
[58] Field of Search ............ 422/64, 67; 364/497, 364/498, 105; 356/435, 434, 398; 23/230 R, 230 B

[56] References Cited

U.S. PATENT DOCUMENTS

| | | |
|---|---|---|
| 3,748,044 | 7/1973 | Liston .......................... 422/67 X |
| 4,234,538 | 11/1980 | Ginsberg et al. ................. 422/64 |
| 4,234,539 | 11/1980 | Ginsberg et al. ................. 422/64 |
| 4,234,540 | 11/1980 | Ginsberg et al. ................. 422/64 |

*Primary Examiner*—Ronald Serwin
*Attorney, Agent, or Firm*—Silverman, Cass & Singer, Ltd.

[57] ABSTRACT

The characteristics of a sample body fluid are determined in a chemical analyzer by sensing the transmittance of light by the sample fluid and reagents during a reaction period. A beam of light is directed onto a cuvette containing the sample body fluid and reagent. A portion of the light is absorbed by the cuvette, the sample fluid and reagent. The remainder of the light is transmitted to a sensor which provides an analog electrical transmittance signal proportional thereto. The analog signal is logarithmically amplified, and is applied to a peak detector. A structure adjacent the cuvette provides a strobe signal such that the analog signal always has a peak amplitude during the strobe signal. The peak detector senses the peak amplitude of the analog signal during the strobe signal and the peak amplitude is converted to a digital value representing absorbance.

47 Claims, 5 Drawing Figures

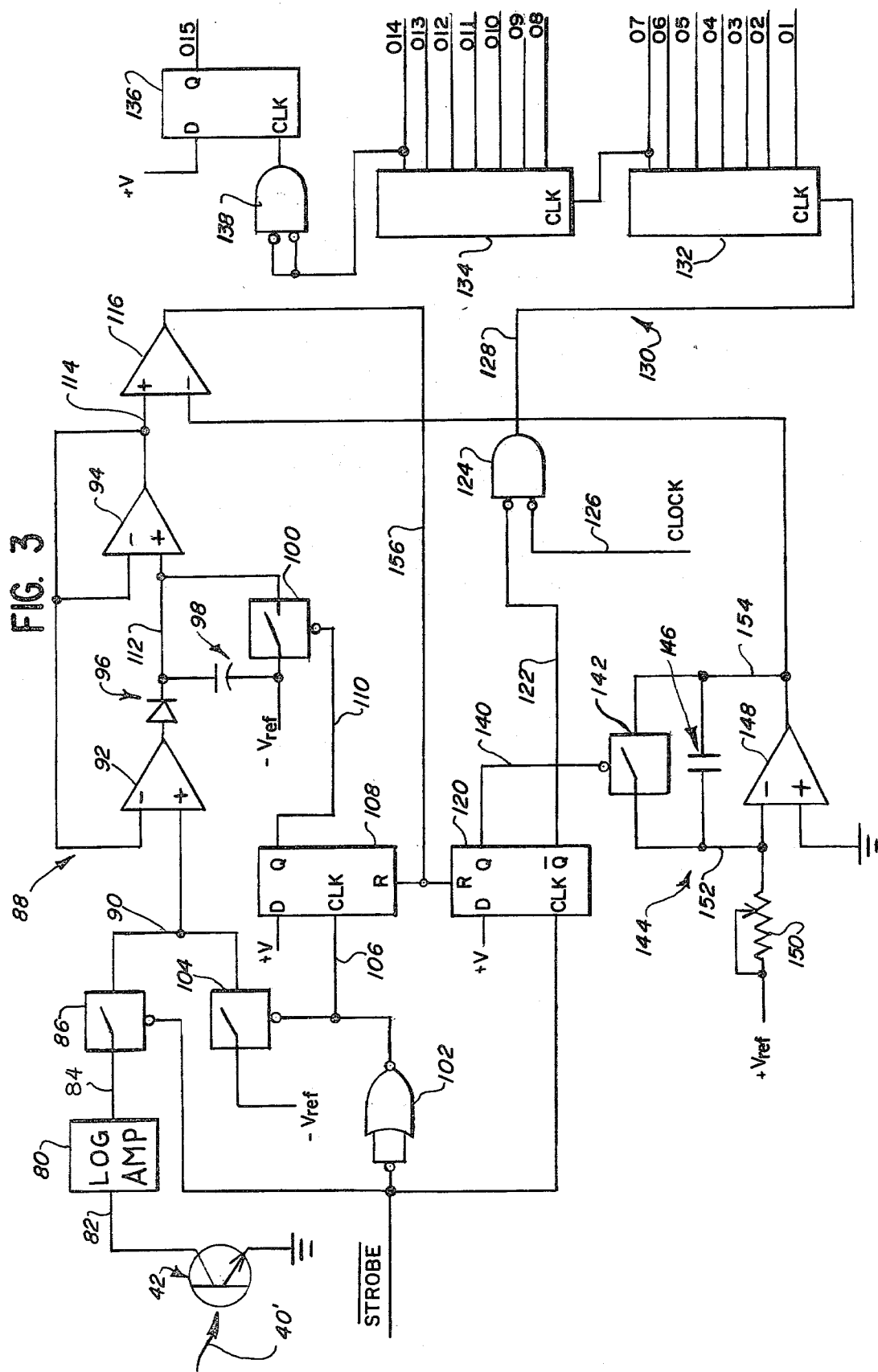

APPARATUS AND METHOD FOR ABSORBANCE MEASUREMENT AND DATA GENERATION

CROSS REFERENCE TO RELATED APPLICATIONS

This invention is related to the subject matter disclosed in the following copending and commonly assigned applications which are incorporated herein by reference:

Apparatus for Monitoring Chemical Reactions and Employing Moving Photometer Means, G. Ginsberg et al, Ser. No. 846,337, filed Oct. 28, 1977, now U.S. Pat. No. 4,234,538 issued Nov. 18, 1980.

Sample and Stat Feeding System and Sample Tray, G. Ginsberg et al, Ser. No. 115,924, filed Jan. 28, 1980, now U.S. Pat. No. 4,276,258 issued June 30, 1981.

Cuvette Washing Apparatus, B. Hodgins et al, Ser. No. 115,692, filed Jan. 28, 1980, now pending.

System and Program for Chemical Reaction Observation with a Moving Photometer, G. Ginsberg et al, Ser. No. 115,734, filed Jan. 28, 1980, now U.S. Pat. No. 4,276,051 issued June 30, 1981.

Fluid Transfer Mechanism, V. Drbal et al, now U.S. Pat. No. 4,276,260 issued June 30, 1981.

Probe Washer, B. Hodgins, Ser. No. 115,625, filed Jan. 28, 1980, now pending.

Variable Stop Syringe, B. Hodgins et al, Ser. No. 115,624, filed Jan. 28, 1980, now U.S. Pat. No. 4,278,086 issued July 14, 1981.

Optical Timing and A/D Conversion Method and Apparatus, Steven N. Kolber et al, Ser. No. 177,092, filed Aug. 11, 1980, now pending.

BACKGROUND OF THE INVENTION

The invention relates to an apparatus and method for measuring repeatedly the absorption of electro-magnetic radiation by a plurality of specimens during a period of time. More particularly this invention concerns an apparatus and method in which each of a plurality of fluid samples or aliquots (portions of the samples) in reaction vessels or cuvettes is subjected to chemical reaction with different reagents. The absorbance of each aliquot repeatedly is determined during the reaction period. The measurement herein involves accurately ascertaining the value of electromagnetic radiation absorption at a particular wavelength by the fluids in the cuvettes and converting the signals from an analog to a digital form so that digital transmission, processing, storage and manipulation may occur.

It is desirable to make such an analysis on a continuous process in which the apparatus continues to operate as long as there are samples to be tested, the old samples and their tested aliquots being replaced by new samples and their aliquots without interruption of the operation of the testing apparatus. Such continuous operation includes one or more photometric measurements on a given aliquot by one or more photometers. It is preferably that the analog transmittance signals received each time a reaction vessel passes through a light beam be converted into digital absorbance signal.

The continuous analyzers of interest typically supply sample portions to the reaction vessels which are monitored by measuring the absorption or transmission of light by the fluids in the cuvettes at a particular wavelength or wavelengths. Sample fluids placed in cuvettes typically are body fluids of a specific patient with one or more tests related to the patient's condition of health being conducted. It is therefore critical that the signals obtained from the fluids in the cuvettes be both accurate and repeatable. The sampling of the peak absorbance signal of each aliquot should be precisely repeatable for each cuvette and each light beam passing through the cuvette.

This application is an improvement over the application Ser. No. 177,092, filed Aug. 11, 1980, now pending. In the prior application the signals derived from the photometer beams passing through the cuvettes must be optimized, WOW in a rotating photometer carrier must be compensated for and the base line of the sample signal established during the dark or non-sample condition must be compensated for. Moreover, a problem presented by measuring the value of the light transmitted by the cuvette and sample fluids contained therein is how to convert the low level millivolt signal which has microvolt accuracy to digital absorbance data having an accuracy of plus or minus one digit with the fixed mechanical limitations of such a device.

The invention herein overcomes these and other disadvantages to provide reliable, accurate and repeatable information on a continuous basis capable of being processed in a high speed digital processor.

SUMMARY OF THE INVENTION

The disadvantages of the prior art cuvette sampling systems and processes are overcome in accordance with the present invention by providing an individual window for each cuvette which is precisely repeatable each time that cuvette coincides with and is sampled by a particular photometric light beam. An analog electronic transmittance signal produced from the photometric light beam is logarithmically amplified and the peak amplitude of the logarithmically amplified signal is detected. The individual windows are aligned with the respective cuvettes so that the peak amplitudes of the signals produced from the photometric light beams always occur during the presence of the window. Each peak amplitude then is converted into digital data indicating the amount of radiant energy which has been absorbed by both the cuvette and reaction sample. The apparatus and method are autocorrecting and require no separate WOW or base line corrections.

BRIEF DESCRIPTION OF THE DRAWING

FIG. 3 is a circuit diagram of the absorbance measurement and data generation structure constructed and operating in accordance with the invention.

DESCRIPTION OF THE PREFERRED EMBODIMENT

The invention herein is described in connection with a chemical analyzer in which sample fluids and particular reagents are inserted in individual cuvettes. Reactions which occur in the individual cuvettes are monitored by measuring the absorbance of light by the individual samples and reagents in the cuvettes. The absorbance of light by the samples and reagents in the cuvettes over a period of time is indicative of the progress of the reaction in the cuvette and depending upon the type of the reagent, the absorbance of the sample and reagent provides data concerning the characteristics of the sample fluid.

The absorbance of the sample fluid is measured by passing a beam of light through the sample within its cuvette and detecting the quantity of transmitted light. The quantity of the transmitted light is logarithmically amplified to provide absorbance information. The peak amplitude of the absorbance information then is measured in conjunction with a window generating structure and the analog peak amplitude is digitized to provide digital absorbance data. By sensing the peak amplitude and by sensing the peak amplitude during a "window" in which the peak amplitude must always occur, an accuracy and repeatability of the absorbance data is obtained which is superior to that of the prior art.

Figure 1:
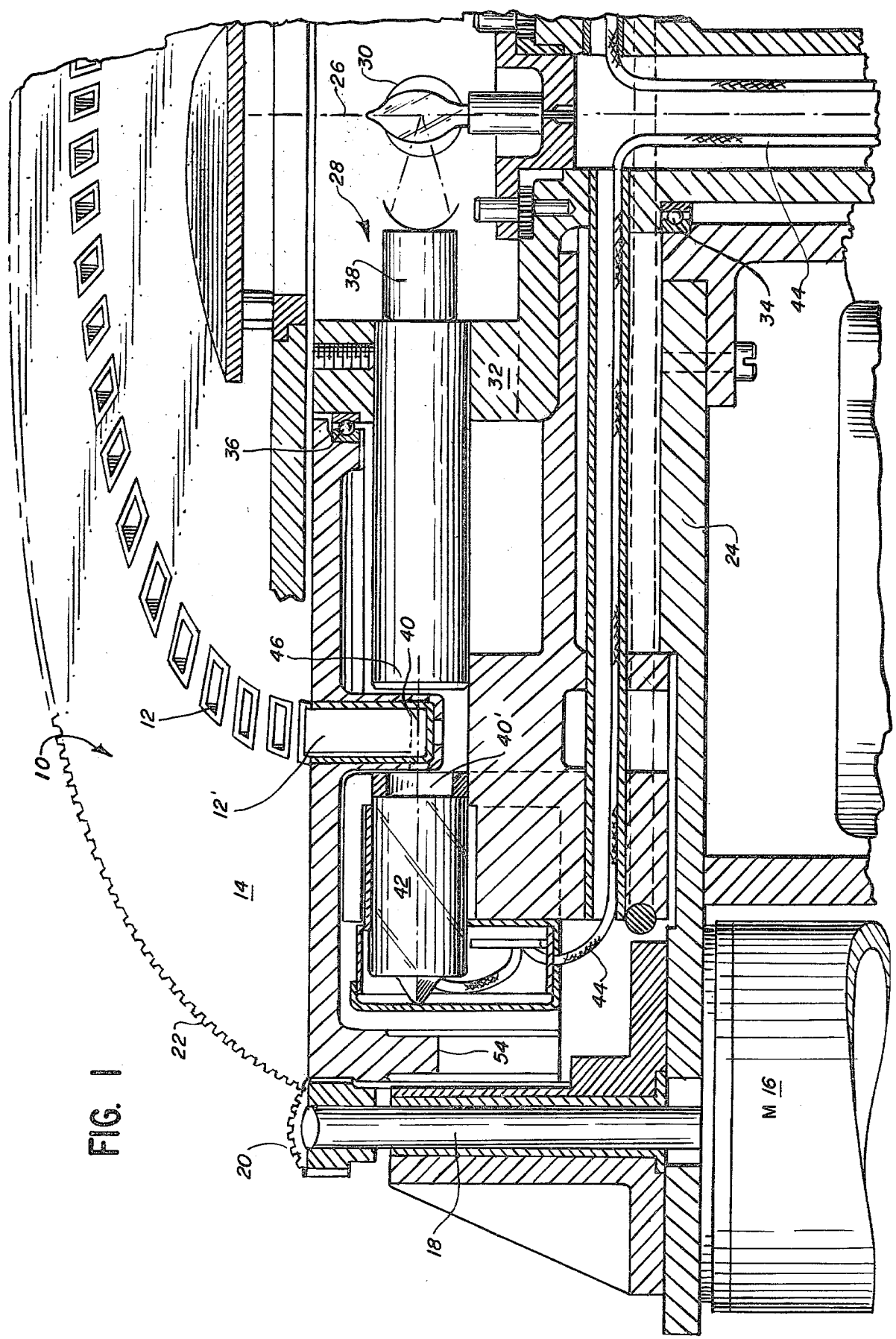
FIG. 1 is a fragmentary median sectional view through the photometric data components of a chemical analyzer constructed according to the invention.

Referring to FIG. 1, a chemical analyzer is designated generally by reference character 10. Chemical analyzer 10 embodies the absorbance measurement and data generation apparatus and method of the invention. Chemical analyzer 10 (partially shown) includes a plurality of cuvettes or reaction vessels 12 which are at least partially transparent and which may be integral with or independently fabricated and installed in a turntable 14 of the analyzer 10. The turntable 14 may be rotated or indexed by a conventional drive mechanism such as a motor 16 having a drive shaft 18 and a pinion gear 20 affixed to one end of the drive shaft 18. The teeth of the pinion gear 20 engage mating teeth 22 on the periphery of the turntable 14. The array of cuvettes 12 will be rotated by being stepped or indexed by the motor 16. As used herein the terms "stepped" and "indexed" include but are not limited to discrete movements, since the turntable 14 and hence the array of cuvettes 12 may be continuously moving slowly without any dwell periods.

The analyzer 10 includes a base plate 24 to which the motor 16 is mounted and with respect to which the array of cuvettes 12 is rotated around an axis 26. The absorbance measurement and data generation unit may be used with a fixed photometer (sensor) having a single beam of light or may be used with fixed plural photometers having a plurality of light beams through which the array of cuvettes 12 is progressively or sequentially passed. Alternatively, the photometer or photometers may be carried on a separate rotor which is rotated around the axis 26 progressively to pass the light beam or beams through the array of cuvettes seriatim.

Indexing the turntable 14 and assuming that the analyzer 10 is performing various functions as the array of cuvettes 12 is rotated past various stations (such comprising for example loading, unloading, and cleaning stations), the array of available and sample containing cuvettes 12 is essentially endless. It is preferable that the beam or beams pass at least once and preferably more than once through each cuvette 12 during each step of the turntable 14. One photometer 28 includes a source of radiation such as a lamp 30 located at the axis 26 of the rotation. The photometer which may be of various constructions is carried by a second rotary member 32 comprising a photometer rotor 32.

The photometer rotor 32 also is driven by drive means (not shown) around the axis 26 on one or a plurality of bearings 34 enabling the rotor to rotate relative to the base plate 24. The cuvette turntable 14 is mounted above the photometer rotor 32 on one or a plurality of bearings 36. A concentric alignment of the photometer rotor 32 and cuvette turntable 14 around the axis 26 provides a precisely repeatable light path through the cuvettes 12, the path being defined by a beam from the lamp 30. Light from the lamp 30 passes into an optical tube 38 carried on the rotor 32. Optical tube 38 includes a lens and has one end proximate to the radiation source or lamp 30 and another proximate to the annular path or pattern traversed by cuvettes 12.

The tube 38 forms a light beam 40 illustrated as passing through a lower portion of a specific cuvette 12' shown in section and through the reaction fluids, if any, in the bottom of the cuvette 12'. The beam of light 40 is partially absorbed by the incident walls of cuvette 12' and by the fluids contained therein, the incident walls of cuvette 12' providing at least partially transparent paths for the light beam. That part of the energy of the light beam 40 which is not absorbed by cuvette 12' and the fluids therein is transmitted as light beam 40' and is received by a photodetector 42. The photodetector 42 generates an analog signal related to the intensity of light remaining in the transmitted beam 40'. The analog signal is coupled to the absorbance measurement and data generation apparatus of the invention by an electrical lead 44.

The absorbance measurement and data generation unit preferably is mounted on and rotated with the rotor 32. Once the analog signals are converted to digital form, they are transmitted from the rotor 32 to a fixed portion of the analyzer 10 physically separated from the rotor 32 where they are analyzed, stored, etc. The transfer of digital signals avoids the inherent difficulties of transmitting analog signals from a rotating element to a fixed element.

The optical tube 38 includes a filter 46 which provides radiant energy of only a particular wave length to be transmitted to the cuvette 12' and thereafter be received by the photodetector 42. The rotor 32 may carry a plurality of photometers similar to photometer 28 each having the optical tube 38 forming a separate beam path directed to respective photodetectors 42. Thus, utilizing a plurality of light beams and photodetectors, the cuvettes 12 may be scanned with a plurality of different photometers each generating a transmittance signal indicative of the received intensity of light at respectively different wavelengths.

As one example of operation, the cuvette turntable 14 may be indexed at a relatively slow rate and may have 120 cuvettes 12 mounted thereon. The turntable 14 is stepped once every six seconds, one full cycle being achieved as a single rotation of the turntable 14 relative to the base plate 24 every twelve minutes. The rotor 32 and photometers rotate around the axis 26 at a speed of one revolution every six seconds, or at a relatively slow speed of ten revolutions per minute or 120 revolutions of rotor 32 for every rotation of the cuvette turntable 14. With eight radially spaced photometers and measurements being made at all times, each cuvette 12 of the cuvette array on the turntable 14 will be photometrically scanned 960 times in a complete cycle relative to the housing or base plate 24. The amount of data generated or the number of times the cuvettes 12 are scanned require that each time a cuvette 12 is scanned by one of the light beams 40, the portion of the signal to be analyzed which is received by the photodetector 42 must be repeatable, that is identical to the signal received on the previous pass of that light beam so that the same light beam or the data will have the necessary accuracy fully to be utilized in the analyzer 10. Further details of a particular analyzer 10 may be found in the application incorporated herein by reference entitled: APPARATUS FOR MONITORING CHEMICAL REACTIONS AND APPLYING MOVING PHOTOMETER MEANS, Ser. No. 846,337, filed Oct. 28, 1977, now U.S. Pat. No. 4,234,538 issued Nov. 18, 1980.

Figure 2A:
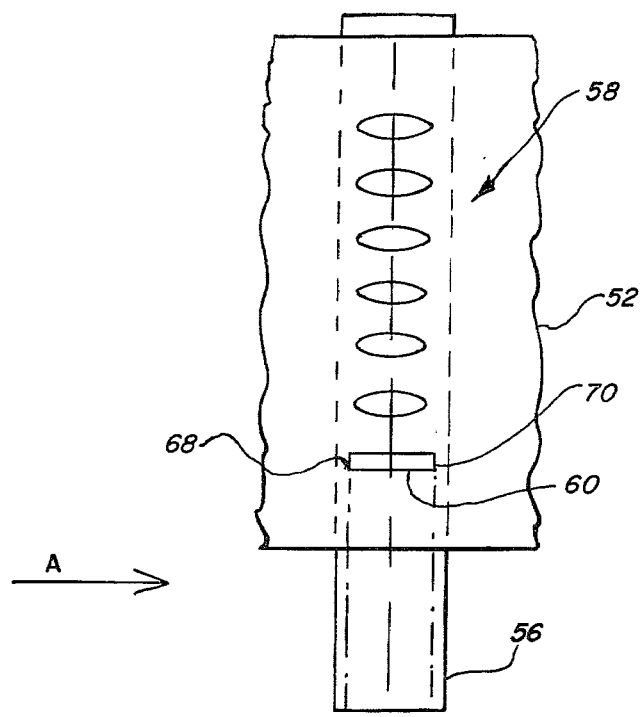
FIGS. 2a and 2b are, respectively, a fragmentary view of a code skirt of a chemical analyzer illustrating a position indicating and window producing structure, and a waveform illustrating the relative intensity of a light beam passing through a cuvette and reaction sample relative to the window structure.
Figure 2B:
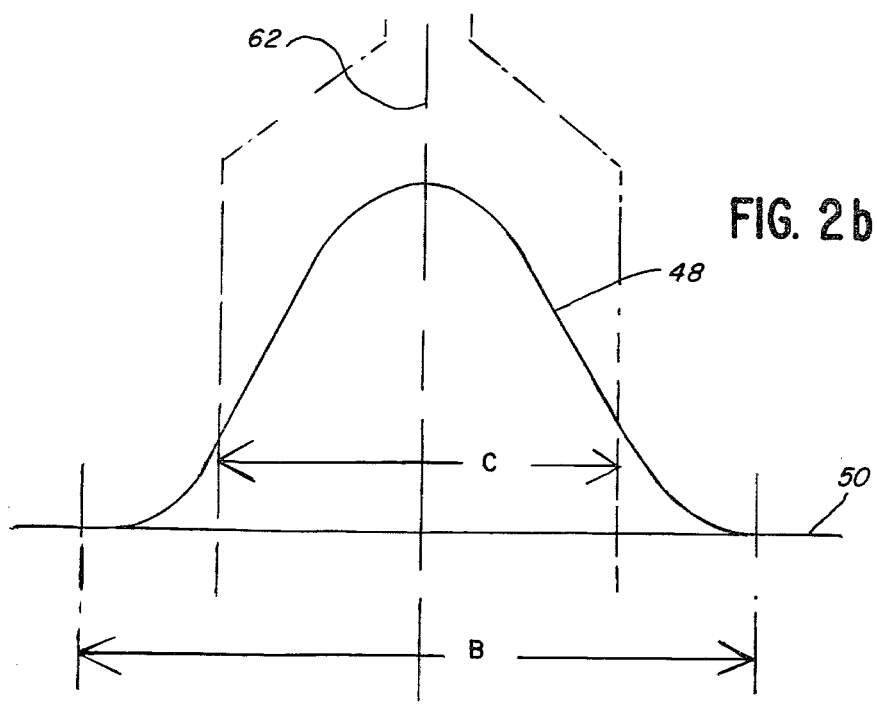

When a cuvette such as 12 containing a sample of some fluid intercepts a passing beam such as 40, some of the radiant energy transmitted through the cuvette and sample such as beam 40' will impinge on the photodetector 42 associated with that beam. In response to the transmitted beam 40', the photodetector 42 will produce a signal which is represented as wave form 48 in FIG. 2b. This wave form 48 is designated $V_{SIG}$. The cuvette 12 along with all the other cuvettes is set into a solid portion of the turntable 14 so that unless the beam 40 finds an opening through the turntable 14 in its path such as through a cuvette 12, no radiant energy from the beam 40 will get to the photodetector 42. This theoretical zero "0" or dark condition is represented by a base-line 50 illustrated below the wave form 48 in FIG. 2b.

The rotor 32 is moving relative to cuvette turntable 14 and the beam 40 from the photometer 28 will pass the position of the cuvette 12 in a direction which is indicated by the arrow A. As the cuvette and beam are swept through one another, assuming that their relative velocity will be constant (which is the preferred form of the rotation of the rotor 32) the wave form 48 will be generated in the photometer circuit. This is an analog electrical transmittance signal and is shown as an idealized smooth signal but will probably vary from the wave form shown, depending upon the light beam alignment with the cuvette 12, beam diameter, noise, speed of rotation or the rotor 32, etc.

The amplitude of $V_{SIG}$ increases from the base line 50 to the peak value of the curve at the time when the beam is in its most favorable alignment with the cuvette 12. The signal $V_{SIG}$ then decreases back again to the base line 50 as the beam passes into the next imperforate wall portion between cuvettes. Thus, the wave form 48 for the particular cuvette will have a total duration as indicated at B, with the horizontal axis being time. In optical and electrical instruments it is not preferable to sample the total wave form 48 encompassed by the time B and hence it is preferable to select a small portion such as is defined by C to sample the peak value occurring during the center portion of the signal $V_{SIG}$. This center portion C may be termed a "window". The peak amplitude of $V_{SIG}$ will vary as the transmittance of the cuvette and sample fluid varies and will also be dependent on the wavelength of the radiant energy of the beam 40. Of course, the window indicated by C may be increased or decreased and/or shifted as desired.

The sample signal illustrated by wave form 48 will be produced in the photodetector when there is relative movement between the cuvette rotor 14 and the photometer 48. Each of the cuvettes 12 in the cuvette array has a specific position and may be identified with the numbers 1, 2, 3, etc. through the entire number of cuvettes in the cuvette array. The numbers of these positions are used to associate the particular cuvette 12 from which specific absorbance data has been obtained. Further, there will be several sets of absorbance measurement data obtained simultaneously due to the plurality of photometers carried by the rotor 32. Preferably, each of these photometers will have a light beam derived from a light tube such as 36 as illustrated in FIG. 1. For equiangular radical spacing on the rotor 32, each photodetector will be generating a wave form similar to 48 for a different cuvette at the same instant of time.

One method of providing information to describe the several cuvette positions is to provide a code skirt or band 52 carried by the cuvette turntable 14 depending from the outer periphery of the turntable 14, but radially inward of the shaft 18 such as at 43 in FIG. 1. The rotor 32 may carry an optical reader 56 (FIG. 2a) on its outer periphery with the code skirt 52 passing between adjacent arms of the optical reader 56 in a conventional manner. The code skirt 52 has a code array 58 of holes punched through the code skirt 52, there being one code array 58 for each of the cuvettes in the cuvette array. The code array 58 indicates the designated number of each cuvette position and the code array 58 is read by passing light therethrough. The arrays 58 and the reader 56 identify each cuvette position so that the analyzer 10 may match the proper signal $V_{SIG}$ with its respective cuvette 12. Each code array 58 includes a strobe hole 60 insuring the physical alignment of the reader 56 with the array 58 so that the correct identification of the array 58 occurs each time it passes a reader 56. The arrays for each of the cuvette positions have a different set of optical holes forming a different optical code for each respective cuvette position.

The signal $V_{SIG}$ represented by the wave form 48 must be positionally repeatable every time an individual cuvette is read by a particular photometer 28 to provide accurate abosrbance measurements of data generation. It is not essential that the sample position C be perfectly centered on the center line 62; however, whether the sample position C is shifted to the right or left as viewed in FIG. 2b, it is essential that the sample position C have the identical alignment with the cuvette every time the individual cuvette is sampled by the photometer.

To obtain the same sampling position C, the "window" as identified earlier, is generated for each of the photometers as each cuvette passes thereby. The strobe hole 60 is physically aligned with its particular cuvette so that the peak amplitude of the signal $V_{SIG}$ always occurs during the "window" provided by the strobe hole 60. The leading edge of the "window" or a STROBE signal will be provided by the leading edge 68 of strobe hole 60 and the trailing edge of the "window" or STROBE signal will be provided by the trailing edge 70 of the strobe hole 60. Alternatively, the timing window may be generated as desired, but so that the sample position of every cuvette is repeatable for each photometer. In utilizing the physical window of the strobe hole 60, the edges 68 and 70 must be clean and precise to provide a sharp leading and trailing edge for the STROBE signal.

Before the operation of the circuit of the absorbance measurement and data generation unit is described, it is beneficial to review the mathematical equations involved.

By definition:

$$\% \text{ TRANS} = 10^{(2-ABS)} \tag{1}$$

where TRANS is the transmittance of the cuvette and sample fluid and where ABS is the absorbance of the cuvette and sample fluid therein.

Inserting relative integer values for ABS (absorbance) we obtain:

$$ABS = 0 \% \; TRANS = 10^2 = 100\% \quad (2)$$

$$ABS = 1 \% \; TRANS = 10^1 = 10\% \quad (3)$$

$$ABS = 2 \% \; TRANS = 10^0 = 1\% \quad (4)$$

$$ABS = 3 \% \; TRANS = 10^{-1} = 0.1\% \quad (5)$$

$$ABS = 4 \% \; TRANS = 10^{-2} = 0.01\% \quad (6)$$

The signal from the photodetector 40 is related to the transmittance as follows:

$$V_{SIG} = V_{TRANS}$$

which is directly related to % TRANS

If the signal $V_{SIG}$ were applied to a logrithmic amplifier, the output of the logrithmic amplifier would be:

$$V_{OUT} = \log [V_{TRANS}] \quad (8)$$

$$V_{OUT} = \log [10^{(2-ABS)}] \quad (9)$$

$$V_{OUT} = -ABS + CONSTANT \quad (10)$$

$$V_{OUT} = -ABS + CONSTANT = V_{ABS} \quad (11)$$

Thus, by applying $V_{SIG}$ to a logrithmic amplifier, we may obtain a signal $V_{ABS}$ which is directly related to absorbance of a cuvette and the sample fluid contained therein. Thus, for relative integer values of absorbance, the voltage output by the logrithmic amplifier will be those same relative integer values. Of course, the actual voltages obtained from the logarithmic amplifier may vary as desired, but for descriptive purposes hereinafter the relative integer values of 0, 1, 2, 3 and 4 will be used. In the preferred embodiment it is intended that the sensitivity of the absorbance measurement and data generation unit have an absorbance range of these integer values.

The use of a logarithmic amplifier to amplify the $V_{SIG}$ from the photodetector 42 has advantages in that the output of the logarithmic amplifier $V_{ABS}$ has rather large values which are directly related to the absorbance characteristics of the cuvette and fluid samples. This together with the remainder of the electronics of the unit provide for an autocalibration of the unit and further eliminates the need for base line correction, WOW correction of the rotating turntable 14 and rotor 32, etc.

Figure 4:
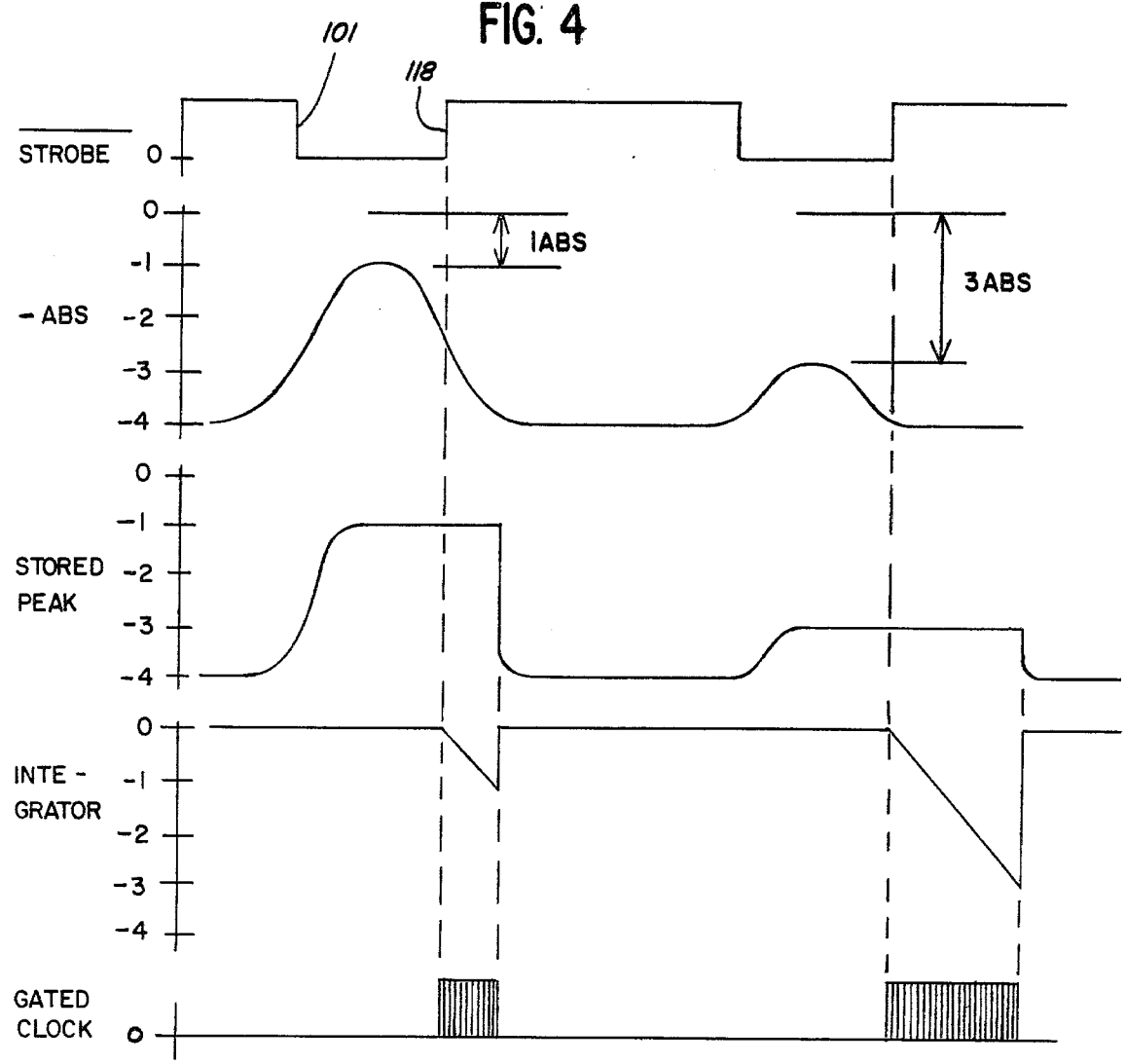
FIG. 4 is a chart illustrating the timing of the operation of the circuit of FIG. 3.

Referring now to FIGS. 3 and 4,, photodetector 42 is indicated as being a phototransistor receiving light in the form of light beam 40'. Photodetector 42 is connected to log amplifier by lead 82. The output of log amplifier 80, $V_{ABS}$, occurs on lead 84 connected to normally open, solid state, switch 86. The open terminal of switch 86 is connected to peak detector 88 by lead 90.

Peak detector 88 includes differential amplifiers 92 and 94, diode 96 and capacitor 98. Normally open switch 100 is connected across capacitor 98, and when closed between the absorbance measurement cycles discharges capacitor 98. The output of the peak detector 88 is the output of amplifier 94 indicated on the curves of FIG. 4 as the signal STORED PEAK.

The peak detection portion of the absorbance measurement and data generation cycle is commenced with the beginning of the "window" represented by the signal inverted STROBE or $\overline{STROBE}$ going from a high (1) to a low (0) logic level and producing a negative edge 101. A "0" applied to switch 86 closes the same, applying the signal $V_{ABS}$ to the normal input of amplifier 92. The "0" signal applied to the inputs of Nor gate 102 connected as an inverter, applies a "1" to normally open switch 104 through lead 106, maintaining switch 104, open, and applies a positive edge to the clock input of flip-flop 180. Flip-flop 108 in turn provides a "1" from its Q output to normally open switch 100 through lead 110 which opens switch 100. Thus, the negative edge of $\overline{STROBE}$ applies $V_{ABS}$ to peak detector 88 and enables the peak detection of that signal.

The peak detection of $V_{ABS}$ occurs by amplifier 92 charging capacitor 98 through diode 96. The output of amplifier 92 is represented by the curve —ABS of FIG. 4. The voltage on lead 112 which is the common connection of the cathode of diode 96, the charged electrode of capacitor 96 and the normal input of amplifier 94 and output of amplifier 94 on lead 114 are represented by the curve STORED PEAK of FIG. 4. This stored signal is fed back to the inverted inputs of both amplifiers 92 and 94 and further is applied to the normal input of comparator 116 formed of a differential amplifier.

As may be seen in FIG. 4, the voltage of —ABS charges positively from some negative voltage such as $-V_{REF}$ to a peak voltage of —1 indicating an integer value of absorbance of 1. The STORED PEAK signal follows the rising edge of the —ABS signal to the peak thereof at —1 but then remains constant as the signal —ABS declines. Thus, the normal input of comparator 116 is maintained at the peak amplitude of the signal indicating the absorbance of the cuvette and fluid sample contained in the cuvette.

The end of the "window" then is reached as is indicated by the rising edge 118 of $\overline{STROBE}$ (FIG. 4). When $\overline{STROBE}$ goes to a "1" state switch 86 opens and switch 104 closes applying $-V_{REF}$ to the normal input of amplifier 92. Switches 86 and 104 may be thought of as a single pole, double throw switch alternately applying $V_{ABS}$ and $-V_{REF}$ to the normal input of amplifier 92. Flip-flop 108 has a negative edge applied to the clock input thereof, which does not change the output Q to switch 100; switch 100 remains open maintaining the signal on lead 112 and as a consequence thereof the stored peak signal on lead 114.

The rising edge 118 of $\overline{STROBE}$ is applied to the clock input of flip-flop 120 causing the $\overline{Q}$ output thereof to go from a "1" to "0" and the Q output to go from a "0" to a "1". The $\overline{Q}$ output appearing on lead 122 enables gate 124 to pass therethrough a high frequency, pulsed clock signal occurring on lead 126. The output of gate 124, GATED CLOCK of FIG. 4., is connected by way of lead 128 to the clock input of a 15 bit binary counter 130 comprising two seven bit binary counters 132 and 134, and a flip flop 136 connected to counter 134 through gate 138. The clock input of counter 134 is connected to the output 07 of counter 132. The clock input of flip flop 136 is connected to the output 014 of counter 134 through gate 138. Counter 130 counts the number of pulses of the high frequency pulsed clock signal occurring on lead 126 during the period while the $\overline{Q}$ output of clock 120 is at a "0" state. As will be described this period is proportional to the absorbance of the cuvette and sample.

When the Q output of flip flop 120 goes to a "1", at edge 118, it applies a "1" by way of lead 140 to normally open switch 142. Switch 142 opens enabling integrator 144 to begin charging negatively and linearly with time, from about a relative integer value "0". Integrator 144 includes capacitor 146, differential amplifier 148 and variable resistor 150. The normal input of amplifier 148 is connected to ground while the inverted input of amplifier 148 is connected through lead 152 and variable resistor 150 to $V_{REF}$. The output of amplifier 148, INTEGRATOR in FIG. 4, is connected by way of lead 154 to the other side of capacitor 146 and the inverted input of comparator 116. Thus, when the $\overline{STROBE}$ signal obtains its trailing edge 118 (FIG. 4), both the GATED CLOCK signal is provided and the INTEGRATOR begins charging negatively.

When the voltage level of the INTEGRATOR signal on lead 154 equals the voltage level of the STORED PEAK signal on lead 114, comparator 116 produces a RESET signal on lead 156 to reset the Q and $\overline{Q}$ outputs of both flip flops 108 and 120. Three things then occur.

First, the "0" on the Q output of flip flop 108 closes switch 100, short-circuiting the charge on capacitor 98 and applying a $-V_{REF}$ to both electrodes thereof. This changes the output of amplifier 94 to about the $-V_{REF}$ voltage.

Second, the $\overline{Q}$ output of flip flop 120 going to "1" disables gate 124 and prevents any further pulses from being applied to counter 120 through lead 128. Counter 130 stops counting.

Third, the Q output of flip flop 120 going to "0" closes switch 142 and short circuits capacitor 146 of integrator 144. Integrator 144 ceases its negative charging and the output of amplifier 148 is at about $+V_{REF}$. This completes one absorbance measurement and data generation cycle.

Thus, the absorbance measurement and data generation unit provides a digital signal in the form of the outputs 01 through 015 of counter 130 which are directly related to the peak value of the beam 40' transmitted through the cuvette and the fluid sample contained in the cuvette. The peak amplitude of the signal has been detected and stored by the peak detector 88 and a digital value has been provided proportional thereto by comparing the amplitude to a signal which changes linearly with respect to time.

The voltage $-V_{REF}$ should be lower than the lowest voltage which may be received from sensor 42; this provides that the amplifiers 92 and 94 always charge positively from the $-V_{REF}$ signal level. The voltage level $+V_{REF}$ should always be greater than the greatest amplitude expected to be received from photosensor 42 so that integrator 144 always charges negatively from a higher voltage than expected. Other suitable components for biasing and input protecting the illustrated components may be included as desired and the absolute voltage levels may be as desired.

Referring to FIG. 4, the left-hand vertical group of changing wave forms corresponds to a condition where the transmittance through the cuvette and reaction fluids is quite high and the absorbance of the cuvette and reaction fluids contained therein has a relative integer value of $-1$. This group of wave forms illustrates that the GATED CLOCK signal is on for a relatively short period of time. The right hand vertical group of wave forms illustrates the case where there is little transmittance and much absorbance by the cuvette and reaction fluids contained therein. The absorbance in this case is indicated as having a relative integer value of $-3$. It will be seen that the INTEGRATOR signal must charge down to the relative integer value of $-3$ and that therefore the GATED CLOCK signal is on for a much longer period of time. The period of time during which the GATED CLOCK signal occurs and consequently the number of clock pulses which are counted, are directly related to the peak amplitude of the measured absorbance value.

The structure and procedure hereinabove described for the absorbance measurement are almost entirely auto-calibrating. The only variable component, illustrated in FIG. 3, is the variable resistor 150 used to set the voltage from which integrator 144 charges negatively. Thus, the present invention provides a simplicity of operation and avoids the need for corrections due to mechanical, electrical and optical imperfections in the turntable 14 and photometer rotor 32.

Modifications and variations of the present invention are possible in light of the above teachings. It is, therefore, to be understood that within the scope of the appended claims, the invention may be practiced otherwise than as specifically described.

What is claimed and desired to be secured by Letters Patent of the United States is:

1. A method of generating reaction effect data derived by directing a beam of radiant energy through a plurality of cuvettes containing reaction samples, and the cuvettes being partially transparent, the method comprising:
   A. scanning the cuvetes seriatim with the beam;
   B. sensing the unabsorbed radiant energy which is transmitted through each cuvette and its reaction sample and generating an analog transmittance signal therefrom;
   C. providing a strobe signal having a period, the strobe signal being timed such that the analog transmittance signal always is at a peak amplitude during the strobe period;
   D. logarithmically amplifying said analog transmittance signal to provide an analog absorbance signal;
   E. detecting the peak amplitude of the analog absorbance signal during the strobe period;
   F. generating data from the detected peak amplitude indicative of the amount of radiant energy which has been absorbed by each cuvette and reaction sample.

2. The method as claimed in claim 1 in which providing a strobe signal includes providing for every cuvette a physical window aligned with that cuvette and the method includes determining the presence of the window.

3. The method as claimed in claim 1 in which the generating of data is effected in a manner to result in digital data.

4. The method as claimed in claim 1 in which detecting the peak amplitude includes charging a capacitor positively from a negative reference voltage.

5. The method as claimed in claim 4 in which generating data includes charging an integrator negatively from a positive reference voltage.

6. The method as claimed in claim 5 in which generating data includes counting the number of pulses of a pulsed clock signal from the end of the strobe period until the voltages on the capacitor and integrator are equal.

7. The method as claimed in claim 6 in which generating data includes comparing the voltages on the capacitor and integrator and producing a reset signal when those two voltages are equal.

8. The method as claimed in claim 5 in which detecting the peak amplitude includes maintaining the detected peak amplitude while charging the integrator negatively.

9. The method as claimed in claim 6 including discharging the capacitor and integrator after the voltages thereon are equal and until the next following strobe period.

10. The method as claimed in claim 1 in which detecting the peak amplitude includes detecting a negative reference voltage between strobe periods.

11. A method of obtaining data relating to the absorbance of a beam of radiant energy of a predetermined wavelength in a plurality of at least partially transparent reaction vessels, each vessel containing a reaction sample of an individual character relative to the other reaction samples in the other reaction vessels, the beam of radiant energy having an optical axis, the beam being passed relative to all of the vessels to scan the same seriatim, the amount of energy remaining in the beam after transmission through each reaction vessel being measured, the method comprising:
  A. repeatedly passing said reaction vessels through said optical axis in a plurality of cycles;
  B. generating a train of transmittance signals by said passage, each signal being related to the absorbance of a respective vessel and contents, the transmittance signals each being generated when the reaction vessel individual thereto is substantially coincident with said optical axis;
  C. providing a plurality of strobe generating means equal in number to said sample vessels and each being individual to a vessel and moving at least one strobe generating means in synchronism with the vessels relative to said optical axis;
  D. generating a strobe signal having a period timed so that the peak amplitude of the transmittance signals always occurs during the strobe period;
  E. logarithmically amplifying said transmittance signals;
  F. detecting the peak amplitudes of the logarithmically amplified analog transmittance signals during the strobe periods; and
  G. generating data from the detected peak amplitudes indicative of the amount of radiant energy which has been absorbed by each reaction vessel and contents.

12. The method as claimed in claim 11 in which generating a strobe signal includes providing for every cuvette a physical window aligned with that cuvette and the method includes determining the presence of the window.

13. The method as claimed in claim 11 in which the generating of data is effected in a manner to result in digital data.

14. The method as claimed in claim 11 in which detecting the peak amplitude includes charging a capacitor positively from a negative reference voltage.

15. The method as claimed in claim 14 in which generating data includes charging an integrator negatively from a positive reference voltage.

16. The method as claimed in claim 15 in which generating data includes counting the number of pulses of a pulsed clock signal from the end of the strobe period until the voltages on the capacitor and integrator are equal.

17. The method as claimed in claim 16 in which generating data includes comparing the voltages on the capacitor and integrator and producing a reset signal when those two voltages are equal.

18. The method as claimed in claim 15 in which detecting the peak amplitude includes maintaining the detected peak amplitude while charging the integrator negatively.

19. The method as claimed in claim 16 including discharging the capacitor and integrator after the voltages thereon are equal and until the next following strobe period.

20. The method as claimed in claim 11 in which detecting the peak amplitude includes detecting a negative reference voltage between strobe periods.

21. Apparatus for generating reaction affect data derived by directing a beam of radiant energy through a plurality of cuvettes containing reaction samples, and the cuvettes being partially transparent, the apparatus comprising:
  A. means for scanning the cuvettes seriatim with the beam;
  B. means for sensing the unabsorbed radiant energy which is transmitted through each cuvette and its reaction sample and generating an analog transmittance signal therefrom;
  C. means for providing a strobe signal having a period, the strobe signal being provided such that the analog transmittance signal always is at a peak amplitude during the strobe period;
  D. means for logarithmically amplifying said analog transmittance signal;
  E. means for detecting the peak amplitude of the logarithmically amplified analog transmittance signal during the strobe period;
  F. means for generating data from the detected peak amplitude indicative of the amount of radiant energy which has been absorbed by each cuvette and reaction sample.

22. The apparatus as claimed in claim 21 in which the means for providing a strobe signal include for every cuvette, a physical window aligned with that cuvette and further include reader means for determining the presence of the window.

23. The apparatus as claimed in claim 21 in which the means for generating data include means for generating digital data.

24. The apparatus as claimed in claim 21 in which the means for detecting the peak amplitude include means for charging a capacitor positvely from a negative reference voltage.

25. The method as claimed in claim 24 in which the means for generating data include means for charging an integrator negatively from a positive reference voltage.

26. The apparatus as claimed in claim 25 in which the means for generating data include means for counting the number of pulses of a pulsed clock signal from the end of the strobe period until the voltages on the capacitor and integrator are equal.

27. The apparatus as claimed in claim 26 in which the means for generating data include means for comparing the voltages on the capacitor and integrator and producing a reset signal when those two voltages are equal.

28. The apparatus as claimed in claim 25 in which the means for detecting the peak amplitude include means for maintaining the detected peak amplitude while charging the integrator negatively.

29. The apparatus as claimed in claim 26 including means for discharging the capacitor and integrator after the voltages thereon are equal and until the next following strobe period.

30. The apparatus as claimed in claim 21 in which the means for detecting the peak amplitude include means for detecting a negative reference voltage between strobe periods.

31. An apparatus for obtaining data relating to the absorbance of a beam of radiant energy of a predetermined wavelength through a plurality of at least partially transparent reaction vessels, each vessel containing a reaction sample of an individual character relative to the other reaction samples in the other reaction vessels, the beam of radiant energy having an optical axis, the beam being passed relative to all of the vessels to scan the same seriatim, the amount of energy remaining in the beam after transmission to each reaction vessel being measured and adapted to be utilized to derive the set of absorbance data, the apparatus comprising:
  A. means for repeatedly passing said reaction vessels through said optical axis in a plurality of cycles;
  B. means for generating a train of transmittance signals by said passage, each signal being related to the absorbance of a respective vessel and contents, the transmittance signals each being generated when the sample vessel individual thereto is substantially coincident with said optical axis;
  C. means for providing a plurality of strobe generating means equal in number to said sample vessels and each being individual to a vessel and moving at least one strobe generating means in synchronism with the vessels relative to said optical axis;
  D. the strobe generating means generating a strobe signal having a period chosen so that the peak amplitude of the transmittance signals always occurs during the strobe period;
  E. means for logarithmically amplifying said analog transmittance signals;
  F. means for detecting the peak amplitude of the logarithmically amplified analog transmittance signals during the strobe periods; and
  G. means for generating data from the detected peak amplitudes indicative of the amount of radiant energy which has been absorbed by each cuvette and reaction sample.

32. The apparatus as claimed in claim 31 in which a strobe generating means include for every cuvette, a physical window aligned with that cuvette and further include reader means for determining the presence of the window.

33. The apparatus as claimed in claim 31 in which the means for generating data include means for generating digital data.

34. The apparatus as claimed in claim 31 in which the means for detecting the peak amplitude include means for charging a capacitor positively from a negative reference voltage.

35. The apparatus as claimed in claim 34 in which the means for generating data include means for charging an integrator negatively from a positive reference voltage.

36. The apparatus as claimed in claim 35 in which the means for generating data include means for counting the number of pulses of a pulsed clock signal from the end of the strobe period until the voltages on the capacitor and integrator are equal.

37. The apparatus as claimed in claim 36 in which the means for generating data include means for comparing the voltages on the capacitor and integrator and producing a reset signal when those two voltages are equal.

38. The apparatus as claimed in claim 35 in which the means for detecting the peak amplitude include means for maintaining the detected peak amplitude while charging the integrator negatively.

39. The apparatus as claimed in claim 36 including means for discharging the capacitor and integrator after the voltages thereon are equal and until the next following strobe period.

40. The apparatus as claimed in claim 31 in which the means for detecting the peak amplitude include means for detecting a negative reference voltage between strobe periods.

41. An apparatus for generating data relating to the absorbance of a beam of radiant energy in a plurality of at least partially transparent reaction vessels, each vessel containing a reaction sample of an individual character relative to the other reaction samples in the other reaction vessels, and the beam of radiant energy having an optical axis, the apparatus comprising:
  a circular rotor containing all of the reaction vessels and located so that the beam optical axis is radial of the rotor, the rotor being rotatable so that all of the reaction vessels may be passed through the beam optical axis seriatim;
  photometer means for generating transmittance signals having amplitudes directly related to the amount of energy remaining in the beam after transmission through the reaction vessels with each transmittance signal being related to the absorbance of a respective vessel and contents, the transmittance signals each being generated when the reaction vessel individual thereto is substantially coincident with said optical axis;
  a code skirt carried by the rotor, the code skirt including for every reaction vessel a strobe hole through the code skirt, the strobe holes each being aligned with the reaction vessels to indicate when the beam optical axis is substantially coincident with the respective reaction vessel;
  strobe generating means for generating a strobe signal in response to every strobe hole, the strobe signals each having a period and being timed so that the peak amplitude of the transmittance signals always occur during the strobe period;
  amplifier means for logarithmically amplifying said transmittance signals;
  detector means for detecting the peak amplitudes of the logarithmically amplified transmittance signals during the strobe periods; and
  generator means for generating data from the detected peak amplitudes indicative of the amount of radiant energy which has been absorbed by each reaction vessel and contents.

42. The apparatus as claimed in claim 41 in which the beam of light is generated by a source located coaxial with the center of the rotor.

43. The apparatus as claimed in claim 41 in which the photometer means are rotatable and rotate relative to the rotor.

44. The apparatus as claimed in claim 41 in which the code skirt includes information related to the position of every reaction vessel.

45. The apparatus as claimed in claim 41 in which the generator means generate digital data.

46. The apparatus as claimed in claim 41 in which the detector means include a capacitor which is charged positively from a negative reference voltage by the absorbance signals.

47. The apparatus as claimed in claim 46 in which the generator means include an integrator charging negatively from a positive reference voltage commencing with the end of the strobe period and a counter counting the number of pulses of a pulsed clock signal from the end of the strobe period until the voltages on the capacitor and integrator are equal.

* * * * *